United States Patent [19]

Ernst et al.

[11] Patent Number: 5,403,278

[45] Date of Patent: Apr. 4, 1995

[54] DEVICE AND METHOD FOR TREATING HEMATOMAS AND FALSE ANEURYSMS

[75] Inventors: J. M. P. G. Ernst, Bilthoven; Ernst Janzen, Laren, both of Netherlands

[73] Assignee: Datascope Investment Corp., Montvale, N.J.

[21] Appl. No.: 156,989

[22] Filed: Nov. 23, 1993

Related U.S. Application Data

[63] Continuation of Ser. No. 869,134, Apr. 15, 1992, abandoned.

[51] Int. Cl.⁶ .................... A61B 17/00; A61M 25/00
[52] U.S. Cl. ........................... 604/60; 604/49; 606/213
[58] Field of Search .............. 604/49, 51–53, 604/57, 59, 60, 164; 606/213; 623/1; 128/DIG. 8

[56] References Cited

U.S. PATENT DOCUMENTS

| | | | |
|---|---|---|---|
| 3,016,895 | 1/1962 | Sein . | |
| 3,572,335 | 3/1971 | Robinson . | |
| 3,804,097 | 4/1974 | Rudie | 604/51 |
| 4,340,018 | 6/1983 | Zukowski | 604/51 |
| 4,578,061 | 3/1986 | Lemelson | 604/164 |
| 4,588,395 | 5/1986 | Lemelson | 604/59 |
| 4,619,261 | 10/1986 | Guerriero . | |
| 4,638,803 | 1/1987 | Rand . | |
| 4,708,718 | 11/1987 | Daniels | 604/53 |
| 4,744,364 | 5/1988 | Kensey . | |
| 4,749,689 | 6/1988 | Miyata et al. | 514/21 |
| 4,790,819 | 12/1988 | Li et al. | 604/49 |
| 4,850,960 | 7/1989 | Grayzel | 604/158 |
| 4,852,568 | 8/1989 | Kensey | 623/1 |
| 4,878,906 | 11/1989 | Lindemann et al. | 623/1 |
| 4,890,612 | 1/1990 | Kensey | 606/213 |
| 4,895,564 | 1/1990 | Farrell | 604/164 |
| 4,900,303 | 2/1990 | Lemelson | 604/54 |
| 4,929,246 | 5/1990 | Sinofsky | 606/8 |
| 4,941,874 | 7/1990 | Sandow et al. | 604/60 |
| 4,950,234 | 8/1990 | Fujioka et al. | 604/60 |
| 4,994,028 | 2/1991 | Leonard et al. | 604/60 |
| 5,021,059 | 6/1991 | Kensey et al. | 606/213 |
| 5,041,090 | 8/1991 | Scheglov et al. | 606/195 |
| 5,061,274 | 10/1991 | Kensey | 606/215 |
| 5,108,407 | 4/1992 | Geremia et al. | 606/1 |
| 5,108,421 | 4/1992 | Fowler | 604/15 |
| 5,129,882 | 7/1992 | Weldon et al. | 604/53 |
| 5,275,616 | 1/1994 | Fowler | 606/213 |

FOREIGN PATENT DOCUMENTS

| | | | |
|---|---|---|---|
| 2641692 | 7/1990 | France . | |
| 8907370.3 | 8/1989 | Germany . | |
| 1509023 | 4/1978 | United Kingdom . | |
| 1569660 | 6/1980 | United Kingdom | 604/57 |
| 8911301 | 11/1989 | WIPO . | |
| 9109641 | 7/1991 | WIPO | 604/49 |

Primary Examiner—Stephen C. Pellegrino
Assistant Examiner—Nancy Mulcare
Attorney, Agent, or Firm—Fitzpatrick, Cella, Harper & Scinto

[57] ABSTRACT

Hematomas and false aneurysms can be treated using a device and method which locate and the provide access to the hematoma or aneurysm. Hemostatic material is then introduced into the hematoma or aneurysm through a new puncture in such a fashion that the hemostatic material does not project into a blood vessel. This can be done by passing a guide wire through a hollow needle, removing the needle, passing a dilator over the guide wire, passing a sheath over the dilator, and then removing the dilator and passing hemostatic material through the sheath into the hematoma or false aneurysm.

19 Claims, 2 Drawing Sheets

DEVICE AND METHOD FOR TREATING HEMATOMAS AND FALSE ANEURYSMS

This application is a continuation of application Ser. No. 07/869,134, filed Apr. 15, 1992, now abandoned.

BACKGROUND OF THE INVENTION

This invention relates generally to the repair of wounds in blood vessels, especially arteries, and to the elimination of the hematomas that result from such wounds.

Those skilled in the art know that occasionally the repair of an artery following a medical procedure such as a catheterization procedure is not totally successful. As a result, the arterial wall is not completely sealed and blood is permitted to escape from the artery into the surrounding tissue. The escaping blood, while unnoticed at first, begins to permeate the surrounding tissue forming an increasingly large hematoma. This condition is referred to as a false aneurysm.

Although a false aneurysm may spontaneously correct itself, often it does not. In the past, when it did not spontaneously correct itself, surgical intervention was called for to repair the artery and to relieve and drain the hematoma.

A device and method for sealing holes in arteries by pressing a plug of collagen or some other hemostatic material over the hole and against the outside of the artery wall is described in co-pending application Ser. No. 746,339, assigned to Datascope Corp., assignee of this application.

SUMMARY OF THE INVENTION

The instant invention provides a new and improved method and apparatus to cure these false aneurysms, repair the arteries and eliminate the hematomas by causing resorption of the blood, all without surgery. In general terms, this invention involves inserting hemostatic material, preferably collagen, into the hematoma. The collagen, it has been found, simultaneously causes resorption of the blood in the hematoma and sealing of the arterial wound. Of course, other hemostatic materials could be used, for example, calcium alginate and oxidized cellulose.

In accordance with the instant invention, the false aneurysm is first accurately located, perhaps by use of contrast medium and well known x-ray techniques, and then an angiographic needle is inserted into the region where the blood has collected. The needle is followed by a guide wire and then by a sheath/dilator-type apparatus. Once the sheath is in place, one or more charges of hemostatic material, preferably collagen, are inserted into the hematoma. It has been found that collagen inserted into the hematoma simultaneously causes resorption of the blood in that hematoma and repair of the wound in the arterial wall.

DETAILED DESCRIPTION OF THE INVENTION

Figure 1:
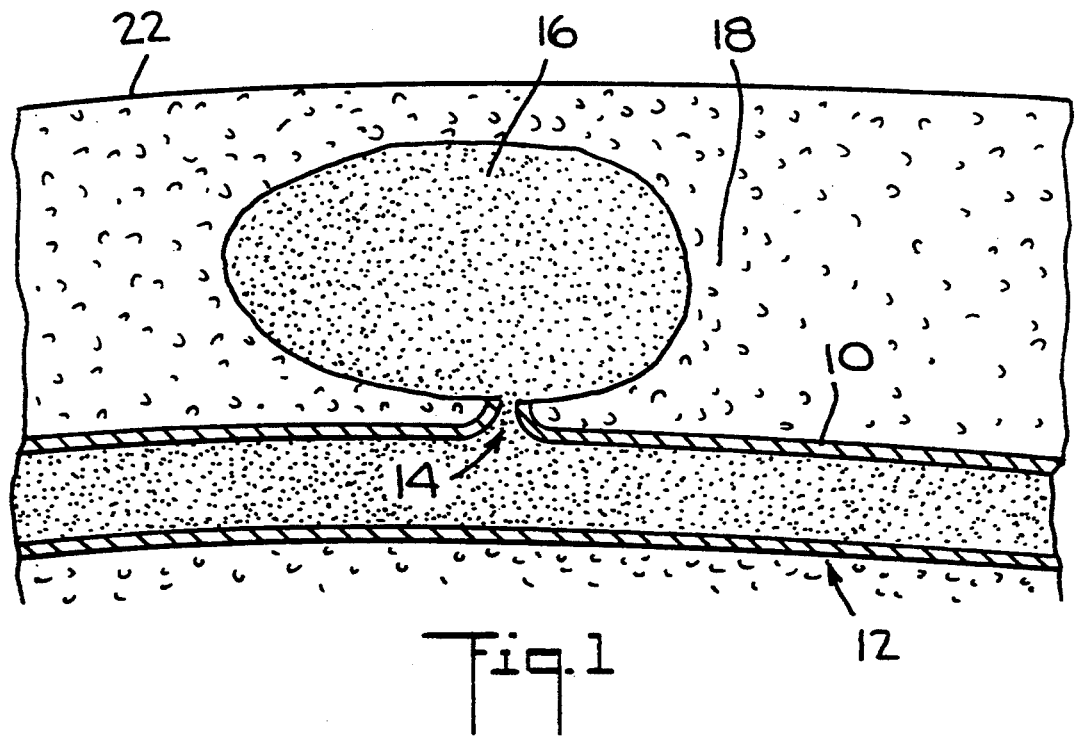
FIG. 1 is a schematic cross sectional view of a false aneurysm which the instant invention is designed to treat.

As best seen in FIG. 1, the wall 10 of a blood vessel 12, most often the femoral artery, has an opening 14 therein. That opening might be the result of an injury to the body of the patient, a weakness in the wall itself or any number of other conditions. Most commonly, it will be the result of an inadequate repair of the puncture hole following an angiographic or other invasive procedure.

As a consequence of there being an opening 14 in the artery wall 10, blood may escape from the artery and form a pool or hematoma 16 in the tissue 18 surrounding the opening, as is depicted in FIG. 1. In accordance with the instant invention, when it is decided that spontaneous repair is not likely to relieve the condition, the position of the hematoma is first located. If necessary, this can be accomplished through the use of contrast medium and x-ray techniques.

An angiographic needle 20 is then inserted through the skin 22 and into the pool of blood 16. Proper positioning of the needle 20 in pool 16 may be confirmed when blood begins to emerge from the end of the needle. If the damaged blood vessel is an artery, for example the femoral artery, proper positioning of the needle will frequently be indicated by pulsatile spurting of blood from the needle.

Figure 2:
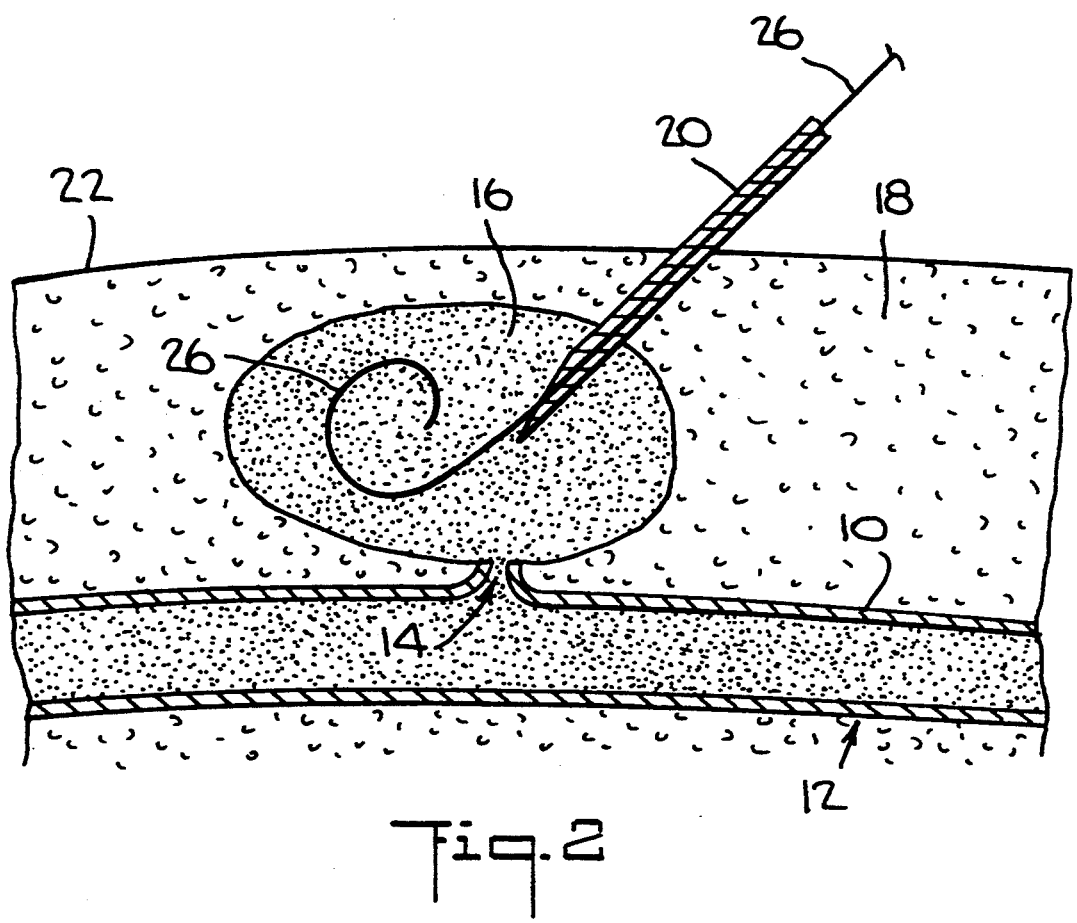
FIG. 2 is a schematic cross sectional view of the false aneurysm of FIG. 1, showing an angiographic needle and a guide wire having passed into the pool of blood that has escaped from the artery.
Figure 3:
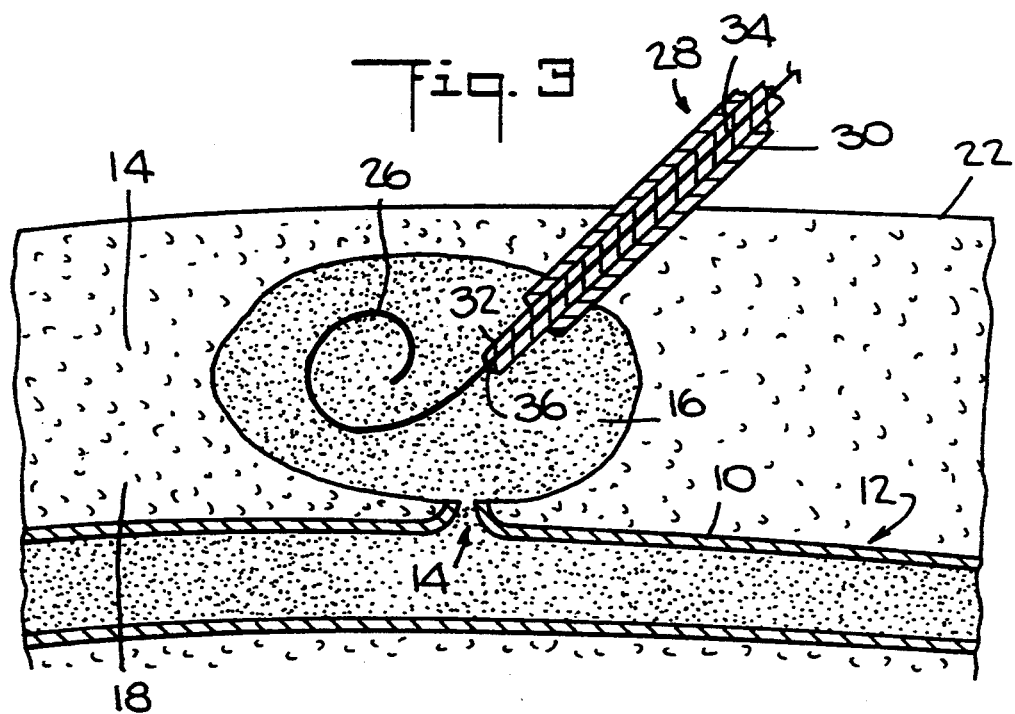
FIG. 3 is a schematic cross sectional view of the false aneurysm of FIG. 1, showing a sheath/dilator-type device having been passed over the guide wire into the pool of blood forming the hematoma.
Figure 4:
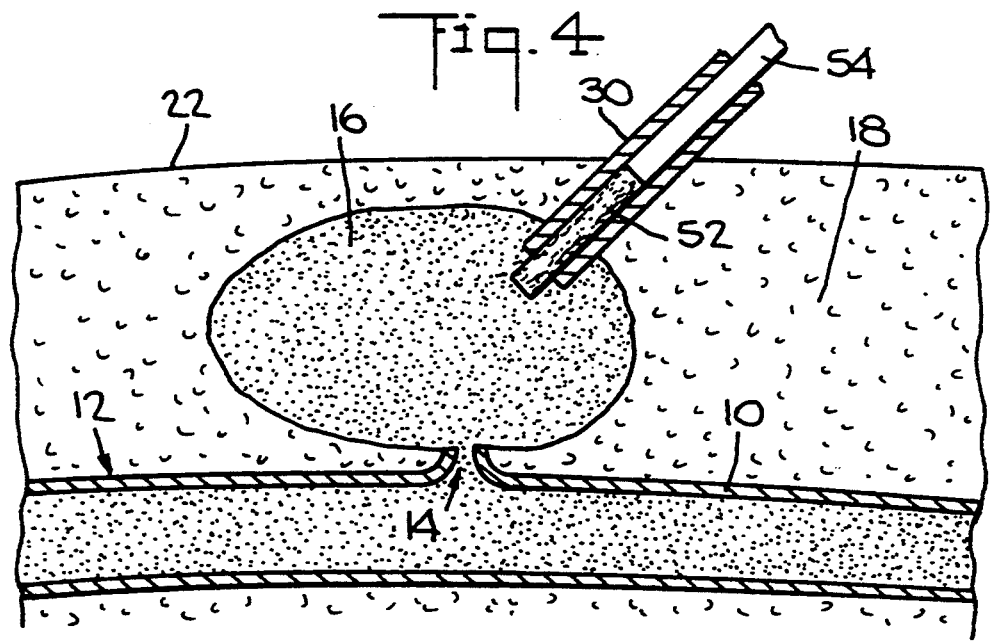
FIG. 4 is a schematic cross sectional view of the false aneurysm of FIG. 1, showing a collagen plug prepared for insertion into the hematoma.
Figure 5:
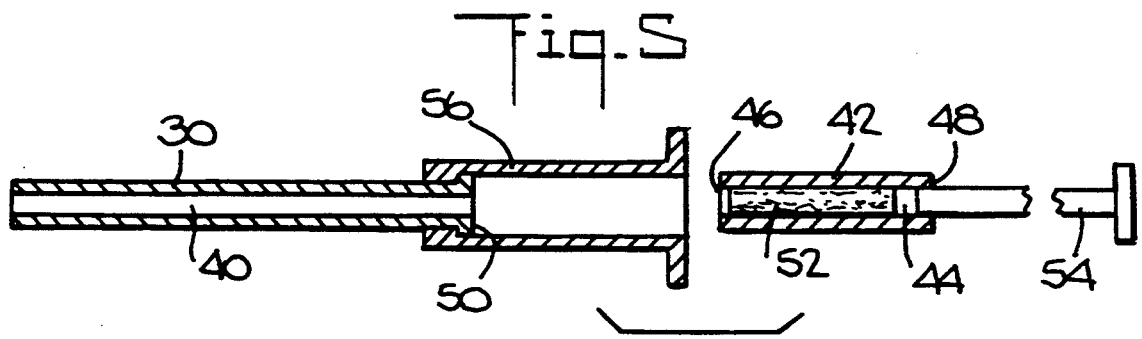
FIG. 5 is a cross sectional view of a device useful in practicing the instant invention.

Once it has been confirmed that needle 20 has been properly positioned in blood pool 16, the artery 12 is clamped, as by application of digital pressure, well above the insertion site. A guide wire 26, preferably one with a 360° bend, is inserted through needle 20 as is depicted in FIG. 2. The needle is then removed, leaving the guide wire in place.

While the artery remains clamped, a sheath/dilator-type device 28 is then passed over the guide wire into hematoma 16. Sheath-dilator 28 is comprised of a sheath 30 and a dilator 32. Dilator 32 preferably has a channel 34 that runs its entire length, from distal end 36 to its proximal end. Sheath 30 is provided with a through lumen 40 that is large enough to accommodate dilator 32. When the sheath/dilator set 28 is assembled, blunt distal end 36 of dilator 32 protrudes beyond the end of sheath 30. In this assembled condition, set 28 is passed over guide wire 26 into hematoma 16. This is done by feeding the guide wire 26 through channel 34 and causing the sheath-dilator set 28 to follow the path of the guide wire.

Sheath 30 is provided with coupling tube 56 having an inside diameter about the same as the outside diameter of sheath 30. Once sheath 30 is in the hematoma, the guide wire and dilator can be removed, leaving only the sheath and its coupling tube in place. A plug or charge holder 42, having a through passage 44 which runs from its front end 46 to its back end 48, is inserted into coupling tube 56 until it abuts proximal end 50 of sheath 30.

Before holder 42 is inserted into coupling tube 56, a charge or plug of hemostatic material 52 is loaded into passage 44. When the front end 46 of holder 42 abuts exposed end 50 of sheath 30, passage 44 preferably is axially aligned with lumen 40 so that charge 52 can easily be pushed from holder 42 into sheath 30.

Once holder 42 is seated in coupling tube 56, a push rod or piston 54 can be used to force plug 50 from passage 44 into lumen 40. Dilator 32 may be serve as the push rod or the push rod may be an entirely independent element. Push rod 54 may be seated within passage 44 as part of a holder assembly before holder 42 is inserted into coupling tube 56, or, alternatively, holder 42 may be inserted into coupling tube 56 first with push rod 54 being inserted into passageway 44 thereafter. Also, while it is preferable to have holder 42 preloaded with a collagen plug, that is not absolutely necessary.

After the plug 50 of hemostatic material has been pushed from passageway 44 into lumen 40, continued application of axial force on push rod 54 causes plug 50 to move through lumen 40 and out of the sheath into the pool of blood 16. Then, in the preferred method of practicing this invention, push rod 54 is removed and holder 42, now empty, is replaced with a second preloaded holder having a new charge of hemostatic material. This second charge is then pushed out of its holder, through lumen 40 and out into hematoma 16 in the same way as was done with the first charge.

While sizes may vary depending upon many factors, it has been found that an 8 or 9 French sheath works well to deliver collagen charges of about 70 mg. Of course, if larger charges are used, fewer of them may be needed. Obviously, the number of charges required to alleviate any given condition will vary, depending upon a number of different factors, including the size of the charges of hemostatic material.

It has been found that the most desirable hemostatic material to use in practicing the instant invention is long loose collagen fibers. It is believed that because such fibers present a very large contact area with the blood in the hematoma, the clotting action they tend to promote is initiated very rapidly.

In the preferred method of practicing the instant invention, after the first two charges have been inserted, the physician waits a few seconds, perhaps ten or fifteen, and then slowly releases the clamping pressure. If the spurting of the blood has stopped, he inserts two more plugs of hemostatic material. If pulsatile spurting persists, three or four or more additional plugs are inserted.

Once all bleeding has stopped and the patient is established as dry, sheath 30 is removed and a conventional pressure dressing can be applied.

It should be understood that, although the above description reflects the preferred manner of practicing the subject invention, those skilled in this art will readily appreciate that many other methods and apparatuses could be used without departing from the basic invention herein disclosed. Basically, the subject invention involves alleviating false aneurysms and hematomas by inserting an hemostatic material, such as collagen, into the region where the blood has collected.

We claim:

1. A method of treating a hematoma comprising the steps of:
   locating the hematoma;
   obtaining access to said hematoma via a newly-created puncture leading to said hematoma; and
   introducing hemostatic material only into said hematoma through said newly-created puncture.

2. A method according to claim 1 wherein said hematoma is a false aneurysm.

3. A method according to claim 1, further comprising the step of providing a sheath, and wherein injecting of said hemostatic material is through said sheath.

4. A method according to claim 1 wherein said hemostatic material is selected from the group consisting of collagen, calcium alginate and oxidized cellulose.

5. A method according to claim 1 wherein said hemostatic material is injected in at least two separate charges.

6. A method according to claim 1 wherein the step of locating the hematoma comprises inserting a hollow needle therein.

7. A method according to claim 1 wherein the step of locating the hematoma comprises:
   providing a contrast medium;
   introducing said contrast medium into said hematoma; and
   observing said contrast medium in said hematoma using fluoroscopic techniques.

8. A method according to claim 6 further comprising the steps of:
   inserting a guide wire through said hollow needle,
   removing said needle while leaving said guide wire in place,
   passing a dilator over said guide wire,
   passing a sheath over said dilator, and removing said dilator,
   passing said hemostatic material through said sheath into said hematoma.

9. A method for treating a false aneurysm in an artery comprising the steps of:
   locating said false aneurysm,
   clamping said artery upstream of said false aneurysm,
   obtaining access to said false aneurysm through a newly-created puncture,
   inserting a sheath through said newly-created puncture into said false aneurysm, and
   inserting a charge of an hemostatic material through said sheath, only into said false aneurysm, and releasing said clamp.

10. A method according to claim 9 further comprising the step of inserting a second charge of hemostatic material through said sheath before releasing said clamp.

11. A method according to claim 10 further comprising the step of inserting at least one additional charge of hemostatic material after said clamp has been released.

12. A method according to claim 11 further comprising the step of inserting at least another charge of hemostatic material after said clamp has been released.

13. A system for use in treating hematomas which communicate with a blood vessel through an opening in a blood vessel wall, comprising:
   locating means for locating said hematoma;
   accessing means for gaining access to said hematoma after said hematoma has been located by said locating means, and
   passing means for passing hemostatic material through a newly-created puncture, which is not said opening in said blood vessel wall, into said hematoma after said hematoma has been accessed.

14. A system according to claim 13 wherein said means for locating said hematoma comprises a hollow needle.

15. A system according to claim 13 wherein said means for gaining access to said hematoma comprises a sheath having a sheath lumen therein 16. A system according to claim 13 wherein said means for gaining access to said hematoma comprises;

a guide wire, a dilator dimensioned so that said dilator can ride along said guide wire, and a sheath dimensioned to accept said dilator.

17. A system according to claim 16 wherein said means for locating said hematoma comprises a hollow needle.

18. A system according to claim 15 wherein said means for passing hemostatic material into said hematoma comprises a plunger slidably received within said sheath lumen.

19. A system according to claim 13, wherein said hemostatic material comprises at least two charges of hemostatic material.

* * * * *

UNITED STATES PATENT AND TRADEMARK OFFICE
CERTIFICATE OF CORRECTION

PATENT NO. : 5,403,278
DATED : April 4, 1995
INVENTOR(S) : JOSEPH M.P.G. ERNST, ET AL.

It is certified that error appears in the above-indentified patent and that said Letters Patent is hereby corrected as shown below:

COLUMN 1

Line 60, "cross sectional" should read --cross-sectional--;

Line 63, "cross sectional" should read --cross-sectional--; and

Line 67, "cross sectional" should read --cross-sectional--.

COLUMN 2

Line 3, "cross sectional" should read --cross-sectional--; and

Line 6, "cross sectional" should read --cross-sectional--.

COLUMN 3

Line 5, "be" should be deleted;

Line 57, "an" should read --a--; and

Line 64, "to" should read --into--.

UNITED STATES PATENT AND TRADEMARK OFFICE
CERTIFICATE OF CORRECTION

PATENT NO. : 5,403,278
DATED : April 4, 1995
INVENTOR(S) : JOSEPH M.P.G. ERNST, ET AL.

It is certified that error appears in the above-indentified patent and that said Letters Patent is hereby corrected as shown below:

COLUMN 4

Line 26, "and removing said" should be deleted;

Line 27, "dilator," should read --removing said dilator, and--;

Line 38, "an" should read --a--;

Line 58, "means," should read --means;--; and

Line 68, "therein" should read --therein.--.

COLUMN 5

Line 3, "comprises;" should read --comprises:--.

Signed and Sealed this

Nineteenth Day of September, 1995

Attest:

BRUCE LEHMAN

*Attesting Officer*     *Commissioner of Patents and Trademarks*